US011307158B1

(12) United States Patent
Pasca et al.

(10) Patent No.: US 11,307,158 B1
(45) Date of Patent: Apr. 19, 2022

(54) NANOPARTICLES FOR CHEMIRESISTOR SENSORS

(71) Applicant: NANOSCENT LTD., Yaad (IL)

(72) Inventors: Yair Pasca, Kiryat Ata (IL); Katya Kapilov, Karmiel (IL); Maayan Hirsch, Haifa (IL); Sima Israel, Haifa (IL); Yahel Zanti, Menahamia (IL)

(73) Assignee: NANOSCENT LTD., Yaad (IL)

( * ) Notice: Subject to any disclaimer, the term of this patent is extended or adjusted under 35 U.S.C. 154(b) by 0 days.

(21) Appl. No.: 17/495,499

(22) Filed: Oct. 6, 2021

(51) Int. Cl.
G01N 27/12 (2006.01)

(52) U.S. Cl.
CPC .................. G01N 27/127 (2013.01)

(58) Field of Classification Search
CPC ............ G01N 27/127; G01N 33/0047; G01N 33/497; G01N 2033/4975; G01N 33/0027; G01N 27/3278; G01N 27/407
See application file for complete search history.

(56) References Cited

U.S. PATENT DOCUMENTS

2009/0049890 A1 2/2009 Zhong
2010/0225337 A1* 9/2010 Zamborini .......... G01N 27/127
324/693
2015/0076340 A1* 3/2015 Liang ...................... H01J 49/26
250/282
2016/0187280 A1 6/2016 Potyralio
2017/0356869 A1 12/2017 Koenig et al.
2021/0364461 A1* 11/2021 Haick ................... G03F 7/0382

FOREIGN PATENT DOCUMENTS

KR 20160014134 A 2/2016
WO 2010021777 A2 2/2010
WO 2017134247 A1 8/2017

OTHER PUBLICATIONS

Welearegay T.G. et al., "Fabrication and characterisation of ligand-functionalised ultrapure monodispersed metal nanoparticle nanoassemblies employing advanced gas deposition technique", Nanotechnology, Oct. 8, 2018, vol. 29, No. 6, doi:10.1088/1361-6528/aa9f65, XP020324162, pp. 1-13.

* cited by examiner

Primary Examiner — Son T Le
Assistant Examiner — Adam S Clarke
(74) Attorney, Agent, or Firm — The Roy Gross Law Firm, LLC; Roy Gross

(57) ABSTRACT

A nanoparticle characterized by sensitivity to an analyte of interest, and comprising a conductive core in contact with a plurality of ligands bound to the conductive core is disclosed. Additionally, a chemiresistor sensor comprising the nanoparticles of the invention and a method of using thereof such as for detection of an analyte of interest in a gaseous sample are disclosed.

20 Claims, 2 Drawing Sheets

NANOPARTICLES FOR CHEMIRESISTOR SENSORS

FIELD OF THE INVENTION

The present invention generally relates to chemiresistor sensors. More particularly, the present invention relates to nanoparticle for chemiresistor sensors.

BACKGROUND OF THE INVENTION

Chemiresistor sensors are sensors that can detect the presence of volatile compound (VCs). A chemiresistor sensor includes a material or structure that changes its electrical resistance in response to changes in the nearby chemical environment, for example, due to the presence of VCs. Commercial chemiresistor sensors for sensing VCs include a sensing element made from one of: carbon nanotubes, graphene, carbon nanoparticles, conductive polymers and the like. These chemiresistor sensors are sensitive to cleaning and regeneration cycles which are required after each measurement, due to the nonuniformity nature of the sensor's material. Another optional sensor includes metallic nanoparticles cores coated with organic ligands. The organic ligands are bonded with the surface of the metallic core at one end and are configured to be weakly bonded (e.g., interact) to a VC at the other end. The most suitable and widely used cores are nanoparticles of: Au, Pt, Pd Ag and further also alloys consisting of Ni, Co, Cu, Al, Au/Ag, Au/Cu, Au/Ag/Cu, Au/Pt, Au/Pd, Au/Ag/Cu/Pd, Pt/Rh, Ni/Co, and Pt/Ni/Fe.

The most common type of organic ligands that can form a bond with the surface of a metallic particle having one of the above listed metallic cores are thiols (sulfides). Exemplary thiols that can be bonded with the metallic cores include alkylthiols with C3-C24 chains, co-functionalized alkanethiolates, arenethiolate, (3-mercaptopropyl) tri-methyloxysilane, dialkyl disulfides, xanthates, oligonucleotides, polynucleotides, peptides, proteins, enzymes, polysaccharides, and phospholipids. These thiols form relatively stable bonds in comparison with other organic ligands, however they are not stable enough and undergo dissociation over time.

The sensitivity of the chemiresistor sensor results from the chemical and physical properties of both the VC and the sensors' ligands. Specific types of VC's of interest may include volatile organic compounds (VOC) such as Aldehydes and Alkanes that can be indicative of the presence of viruses or other pathogens in an air sample. Other VOCs can be used as bio markers of specific disease such as COVID-19 or lung cancer. An air sample, for example, taken from a human breath includes many types of VCs such as, $N_2$, $O_2$, $CO_2$, $H_2O$, nitrogen oxides (e.g. NO, $NO_2$) and VOCs, such as ketones (e.g. Acetone), Isoprene, alcohol (e.g. Methanol) and many more.

There is a need for a chemiresistor sensor with increased sensitivity to of one or more VOC of interest (e.g. an alkane (C6 and higher alkanes), and/or aldehyde), which are present within the gaseous sample in only minor amounts, (e.g. at a concentration of between a few ppbs to hundreds of ppb) together with additional VCs and/or VOCs.

Aldehydes (e.g. Decanal, Nonanal, Octanal, Heptanal and Hexanal) and alkanes (e.g. Octane, Nonane, Decane, Dodecane) have been reported to be associated with certain disease states, such as SARS-CoV-2 (i.e. COVID-19). Aldehyde production is attributed to cellular oxidative stress in the lung during viral infections, such as COVID-19, leading to accumulation of by-products of oxidation of unsaturated fatty acids, therefore manifested as increase of Aldehydes total concentration in human breath.

Accordingly, there is a need for chemiresistor sensors with increased sensitivity to analytes of interest, such as Aldehydes and Alkanes and optionally other VOCs of interest.

SUMMARY OF THE INVENTION

In one aspect of the invention, there is provided a nanoparticle, comprising a conductive core in contact with a plurality of ligands bound to said core, wherein each ligand comprises a first moiety thereof capable of binding to the core and a second moiety covalently bound to said first moiety; wherein the second moiety is an alkyl-aryl moiety comprising at least 2 aliphatic carbon atoms and the plurality of ligands are assembled to form a shell on top of said core; and wherein said nanoparticle is characterized by sensitivity to an analyte of interest.

In one embodiment, each of the plurality of ligands is bound to the core via the first moiety, and wherein said bound is via a covalent bond and wherein the covalent bond comprises a coordinative bond.

In one embodiment, each core independently comprises a transitional metal, optionally wherein the transitional metal is substantially in an elemental state within said core.

In one embodiment, the ligand is represented by Formula 1:

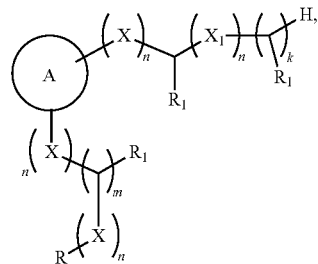

wherein: R represents the first moiety; each R1 independently represents a substituent or H; each X and X1 independently represents a heteroatom, —CHR1-, —CR1R1-, or is absent; A represents an optionally substituted aryl, an optionally substituted heteroaryl, a polycyclic aryl or any combination thereof; n and k are integers each independently ranging from 0 to 5; and m is an integer ranging from 1 to 5.

In one embodiment, the heteroatom is selected from the group consisting of O, S, NH, NR1, PH and PR1 or a combination thereof; and if X1 represents the heteroatom then k ranges between 1 and 5.

In one embodiment, the first moiety comprises thio, carboxy, carbonyl, amino, hydroxy, amide, optionally substituted disulfide, silyl, diazo, heteroaryl, an olefin, phosphate, silyl, phosphine, including any salts, any derivative or any combination thereof.

In one embodiment, the first moiety comprises thio or thiolate, and wherein the alkyl-aryl moiety is represented by Formula 2:

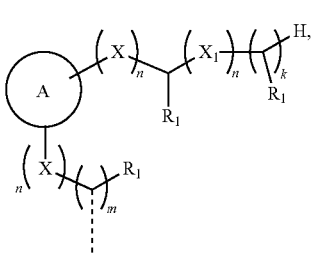

wherein: each R1 independently represents a substituent or H; each X and X1 independently represents a heteroatom, or is absent; A represents an optionally substituted aryl, an optionally substituted heteroaryl, or any combination thereof; the dashed line represents an attachment point to the first moiety; the heteroatom is selected from the group consisting of O, S, NH, and NR1, or a combination thereof; n is an integer each independently being 0 or 1; k is an integer ranging from 0 to 5; m is an integer ranging from 1 to 5; and if X1 represents the heteroatom then k ranges between 1 and 5.

In one embodiment, m and k each independently is 1 or 2.

In one embodiment, the alkyl-aryl moiety comprises an aryl substituted in meta-, or in para-position.

In one embodiment, the alkyl-aryl moiety is represented by Formula 3:

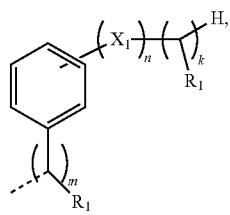

wherein m is 2, and wherein k is between 1 and 3.

In one embodiment, the ligand comprises at least one of:

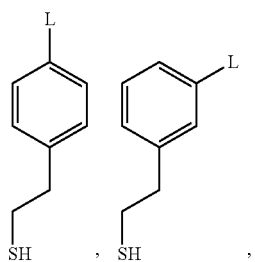

wherein L comprises ethyl or butyl.

In one embodiment, the substituent comprises one or more substituents, wherein each substituent is independently selected from the group consisting of: each independently selected from the group consisting of: $C_1$-$C_6$ alkyl, halo, —$NO_2$, —CN, —OH, —$NH_2$, carbonyl, —$CONH_2$, —$CONR'_2$, —$CNNR_2$, —$CSNR_2$, —CONH—OH, —CONH—$NH_2$, —NHCOR', —NHCSR', —NHCNR', —NC(=O)OR', —NC(=O)NR', —NC(=S)OR', —NC(=S)NR', —$SO_2R'$, —SOR', —SR', —$SO_2OR'$, —$SO_2N(R')_2$, —$NHNR'_2$, —NNR', —NH($C_1$-$C_6$ alkyl), —N($C_1$-$C_6$ alkyl)$_2$, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), amino($C_1$-$C_6$ alkyl), —CONH($C_1$-$C_6$ alkyl), —CON($C_1$-$C_6$ alkyl)$_2$, —$CO_2H$, —$CO_2R'$, —OCOR', —OCOR', —OC(=O)OR', —OC(=O)NR', —OC(=S)OR', —OC(=S)NR', a heteroatom, an optionally substituted cycloalkyl, an optionally substituted heterocyclyl, or a combination thereof, wherein each R' is independently selected from hydrogen, alkyl, alkenyl, aryl, heteroaryl a heteroatom, an optionally substituted cycloalkyl, an optionally substituted heterocyclyl, or any combination thereof.

In one embodiment, the analyte of interest is a volatile organic compound (VOC) selected from an optionally unsaturated C1-C20 aldehyde, and an optionally unsaturated C1-C20alkane, or both.

In another aspect, there is provided a chemiresistor sensor comprising at least two electrodes; and a sensing element electrically connected to the two electrodes and comprising a structure made from a plurality of nanoparticles, wherein each nanoparticle comprises a metal core in contact with a plurality of ligands bound to said core; each ligand comprises a first moiety or a salt thereof capable of binding to the core, and an alkyl-aryl moiety covalently bound to said first moiety; the plurality of ligands are assembled to form a shell on top of said core; and wherein said nanoparticle is characterized by sensitivity to an analyte of interest comprising a volatile organic compound (VOC) selected from an optionally unsaturated C1-C20 aldehyde, and an optionally unsaturated C1-C20alkane.

In one embodiment, the first moiety comprises thio or thiolate, and wherein the alkyl-aryl moiety is represented by Formula 2:

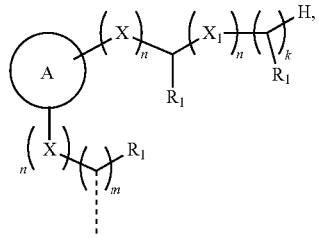

wherein each R1 independently represents a substituent or H; each X and X1 independently represents a heteroatom, or is absent; A represents an optionally substituted aryl, an optionally substituted heteroaryl, or any combination thereof; the dashed line represents an attachment point to the first moiety; the heteroatom is selected from the group consisting of O, S, NH, and NR1, or a combination thereof; n is an integer each independently being 0 or 1; k is an integer ranging from 0 to 5; m is an integer ranging from 1 to 5; and if X1 represents the heteroatom then k ranges between 1 and 5.

In one embodiment, the ligand comprises at least one of:

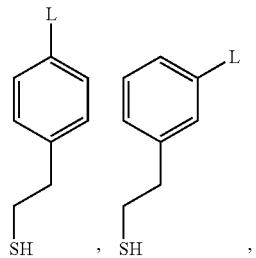

wherein L comprises ethyl or butyl.

In one embodiment, the sensor is configured for selective detection of the analyte of interest within a gaseous sample, wherein a concentration of the analyte of interest within the sample is between 1 ppb and 1 ppm.

In another aspect, there is a method for detection of an analyte of interest in a gaseous sample, comprising: a. exposing the sensor of the invention to the sample comprises a plurality of VOCs; b. providing electricity to the sensor, so as to obtain a plurality of conductivity values generated by the sensor; and c. analyzing said conductivity values, thereby determining the presence of the analyte of interest within said sample, wherein the analyte of interest comprises a VOC selected from an aldehyde, an alkane or both.

In one embodiment, the analyzing step further comprises determining a concentration of the analyte of interest within the sample.

In one embodiment, a concentration of the analyte of interest within the sample is between 1 ppb and 1 ppm.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
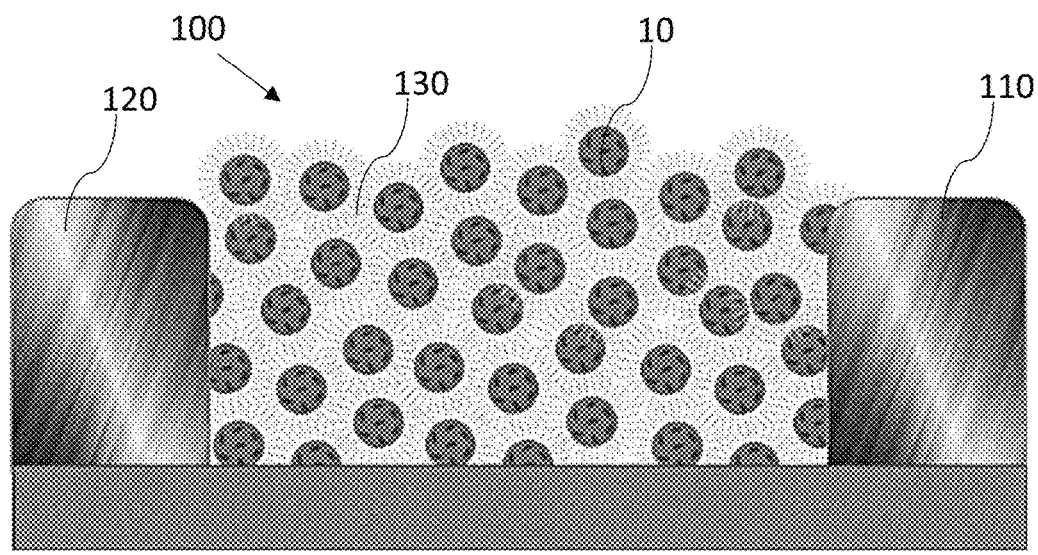
FIG. 1 is an illustration of a chemiresistor sensor according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

Opening Statement

The invention in some embodiments thereof is based on a surprising finding that a chemiresistor sensor comprising a sensing element composed inter alia of nanoparticles comprising a conductive metal core covalently bound to a plurality of alkyl-aryl based ligands, exhibited an unexpected selectivity and/or sensitivity to aldehydes. A chemiresistor sensor based on the nanoparticles of the invention, has been successfully implemented by the inventors for detection of aldehydes and/or long-chain alkanes (C6 and longer alkanes) in a gaseous sample. Some of the nanoparticles disclosed herein, were found to be appropriate for highly selective sensing of aldehydes (such as Decanal, Nonanal, Octanal, Heptanal and Hexanal) and alkanes (such as hexane, nonane, decane, etc.) at low ppb-level.

The FIGS

Reference is now made to FIG. 1 which is an illustration of a chemiresistor sensor according to some embodiments of the invention. A chemiresistor sensor 100 may include: two electrodes 110 and 120 and a sensing element 130 connected to electrodes 110 and 120 and comprising a structure made from the particles 10 discloses herein below. Chemiresistor sensor 100 may be included in a scent recorder. Electrodes 110 and 120 may be connected to a processor (e.g., a chip) that may detect changes in the electrical resistance of sensing element 130 in response to changes in the nearby chemical environment, for example, due to the presence of VCs of interest.

In some embodiments, sensing element 130 may include a plurality of particles 10. Particles 10 may be mixed with a carrier solvent and printed/deposited in order to form sensing element 130. The carrier solvent may be evaporated prior to the use of sensing element 130.

Figure 2:
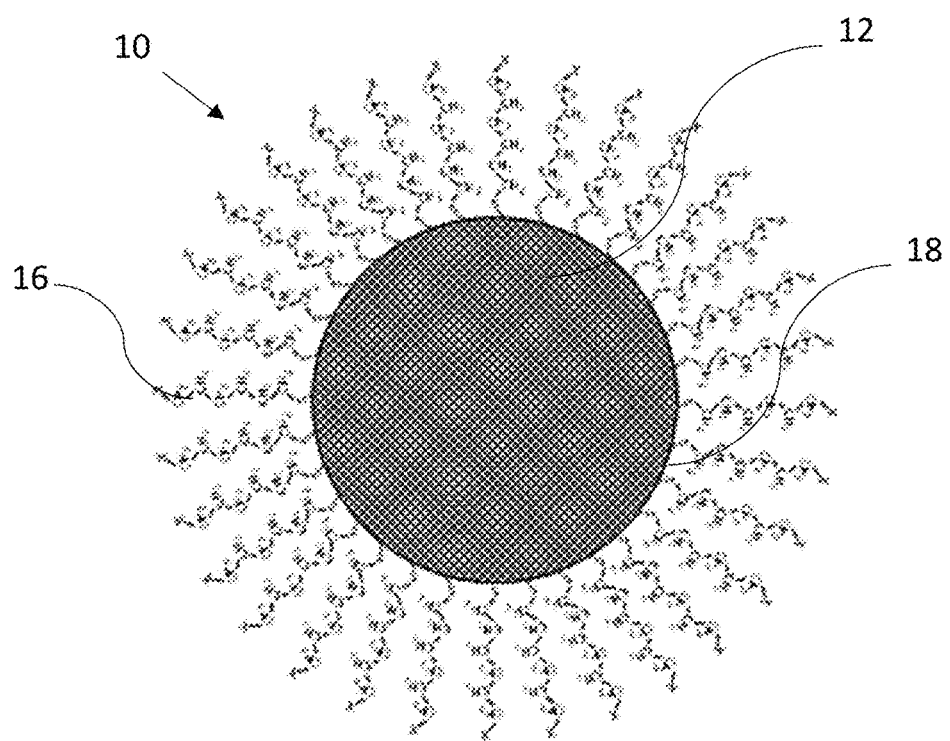
FIG. 2 is an illustration of a particle for chemiresistor sensor according to some embodiments of the invention.
Figure 3:
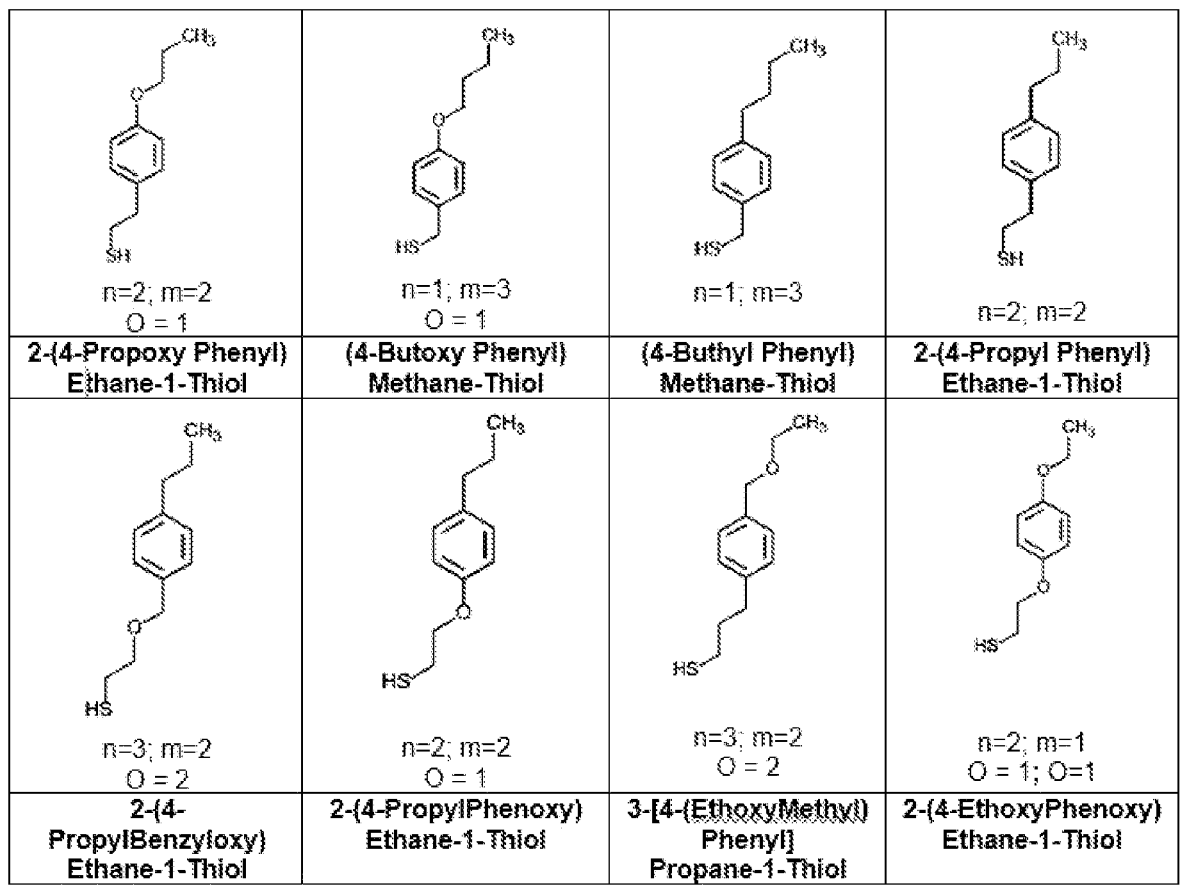
FIG. 3 is a table illustrating optional ligands according to embodiments of the invention.

Reference is now made to FIG. 2 which is an illustration of a nanoparticle 10 according to some embodiment of the invention. Nanoparticle 10 may include a conductive core 12 and a plurality of ligands (e.g. organic ligands) 16 bonded to core 12.

In some embodiments, the nanoparticle of the invention is non-uniformly shaped. In some embodiments, a plurality of nanoparticles of the invention is devoid of a defined shape (e.g. the particles have a random shape). In some embodiments, the nanoparticle of the invention is characterized by substantially spherical shape, elliptical shape, and/or a cylindrical shape. In some embodiments, the shape of the nanoparticle is substantially predefined by the shape of the conductive core.

Core

Conductive core 12 may include any conductive suitable material, for example, a metal (e.g. a metal in an elemental state) and/or any conductive metallic oxide. For example, conductive core 12 may include: one or more transitional metal(s), optionally the transitional metal is substantially in an elemental state within said core. Some nonlimiting examples of transitional metals for conductive core 12 include: Ir, Ir-alloy, IrOx, Ru, Ru-alloy, RuOx Au, Pt, Pd, Ag and further also alloys consisting of Ni, Co, Cu, Al, Au/Ag, Au/Cu, Au/Ag/Cu, Au/Pt, Au/Pd, Au/Ag/Cu/Pd, Pt/Rh, Ni/Co, and Pt/Ni/Fe and any combination thereof. Other conductive metals or metal oxides are well-known in the art.

In some embodiments, each of the nanoparticles of the invention comprises a single conductive core. In some embodiments, each of the nanoparticles of the invention comprises the same conductive core, and the same or different ligand species. In some embodiments, at least a portion of the nanoparticles of the invention have chemically distinct conductive cores and the same or different ligand species.

In some embodiments, the conductive core is characterized by resistivity of less than $10^{-1}$ Ωcm, less than $10^{-2}$ Ωcm, less than $10^{-3}$ Ωcm, less than $10^{-4}$ Ωcm, less than $10^{-5}$ Ωcm, less than $10^{-8}$ Ωcm, less than $10^{-10}$ Ωcm, less than $10^{-12}$ Ωcm, including any range between, when measured at 20° C.

In some embodiments, the metal within the conductive core is in an elemental state, or in an oxidized state (e.g. a metal oxide and/or a metal salt). In some embodiments, at least 90%, at least 93%, at least 95%, at least 97%, at least 99.9%, or 100% including any range between, by weight of the metal within the conductive core is in a form of a metal oxide. In some embodiments, at least 90%, at least 93%, at least 95%, at least 97%, at least 99.9%, or 100% including any range between, by weight of the metal within the conductive core is in an elemental state. As used herein, the term "elemental state" refers to zero oxidation sate of an atom.

In some embodiments, at least 60%, at least 70%, at least 80%, at least 90%, at least 93%, at least 95%, at least 97%, at least 99.9%, or 100% including any range between, by weight of the conductive core is composed of the conductive metal.

In some embodiments, the conductive metal is in a crystalline state. In some embodiments, at least 80%, at least 90%, at least 93%, at least 95%, at least 97%, at least 99.9%, or 100% including any range between, by weight of the conductive metal is in a crystalline state.

In some embodiments, the conductive metal is in an amorphous state. In some embodiments, at least 80%, at least 90%, at least 93%, at least 95%, at least 97%, at least 99.9%, or 100% including any range between, by weight of the conductive metal is in an amorphous state.

In some embodiments, the conductive core comprises an inner portion and an outer portion facing the ambient. In some embodiments, the outer portion is bound to the ligands of the invention. In some embodiments, the inner portion comprises about 97%, about 98%, about 99%, about 99.9%, about 99.99%, about 99.999% of the entire weight and/or entire volume of the conductive core. In some embodiments, the outer portion refers to the outer surface of the conductive core. In some embodiments, the outer portion is in a form of a layer. In some embodiments, the outer portion comprises of one or more (e.g. 2, 3, 5, or 10) atomic layer(s).

In some embodiments, the conductive core comprises a single metal (e.g. a metal in an elemental state, or a metal in an oxidized state). In some embodiments, the conductive core comprises an alloy or a mixture of a plurality of metals (e.g. 2, 3, 4, 5 or more metals). In some embodiments, the conductive core comprises one or more metals in an elemental state and the one or more metals in an oxidized state.

In some embodiments, the inner portion and the outer portion of the conductive core is or comprises one or more metals in an elemental state. In some embodiments, the inner portion is or comprises one or more metals in an elemental state, and the outer portion is or comprises one or more metals in an oxidized state (e.g. conductive metal oxide).

In some embodiments, the inner portion and/or the outer portion of the conductive core is substantially devoid of an organic compound. In some embodiments, the inner portion and/or the outer portion is substantially devoid of a non-conductive metal and/or a non-conductive metal oxide, or a non-conductive metal salt. In some embodiments, the entire conductive core is substantially devoid of: an organic compound, a non-conductive metal, a non-conductive metal oxide, or a non-conductive metal salt including any combination thereof.

In some embodiments, the conductive core is or comprises Au, Pt, Ru, Rh, Ag, Ir, Pd, Ni, Co, Cu, Al including any conductive oxide or any combination thereof. In some embodiments, the conductive core is or comprises a noble metal or an alloy thereof. In some embodiments, the conductive core is or comprises a noble metal oxide. Non-limiting examples of noble metals include but are not limited to: Au, Pt, Ru, Ag, Rh, Ir, and Pd.

In some embodiments, the average cross section size of conductive core 12 may be of at most 100 nm. In some embodiments, the average cross section size of conductive core 12 may be of at most 80 nm. In some embodiments, the average cross section size of conductive core 12 may be of at most 70 nm. In some embodiments, the average cross section size of conductive core 12 may be of at most 60 nm. In some embodiments, the average cross section size of conductive core 12 may be of at most 50 nm. In some embodiments, the average cross section size of conductive core 12 may be of at most 40 nm. In some embodiments, the average cross section size of conductive core 12 may be of at most 30 nm. In some embodiments, the average cross section size of conductive core 12 may be of at most 20 nm. In some embodiments, the average cross section size of conductive core 12 may be of at most 10 nm. In some embodiments, the average cross section size of conductive core 12 may be of at most 5 nm, for example, 1 nm, 2 nm, 3 nm, etc.

In some embodiments, the average cross section size of the conductive core (e.g. of the plurality of nanoparticles of the invention) is between 1 and 100 nm, between 1 and 10 nm, between 10 and 50 nm, between 50 and 100 nm, including any range between. In some embodiments, the average cross section size of the conductive core (e.g. of the plurality of nanoparticles of the invention) is between 1 and 20 nm, between 1 and 10 nm, between 10 and 15 nm, between 15 and 20 nm, between 1 and 5 nm, between 1 and 3 nm, between 3 and 5 nm, between 5 and 7 nm, between 7 and 10 nm, including any range between In some embodiments, the nanoparticles of the invention are characterized by a particle size in a range between 1 and 100 nm, between 1 and 10 nm, between 10 and 50 nm, between 50 and 100 nm, including any range between. In some embodiments, the nanoparticles of the invention are characterized by a particle size in a range between 1 and 5 nm, between 1 and 3 nm, between 3 and 5 nm, between 5 and 7 nm, between 7 and 10 nm, including any range between.

In some embodiments, the term "particle size" refers to average cross section size of the nanoparticles.

In some embodiments, the term "average cross section size" may refer to either the average of at least e.g., 70%, 80%, 90%, or 95% of the particles, or in some embodiments, to the median size of the plurality of nanoparticles. In some embodiments, the term "average cross section size" refers to a number average of the plurality of nanoparticles. In some embodiments, the term "average cross section size" may refer to an average diameter of substantially spherical nanoparticles.

Shell

In some embodiments, the nanoparticle of the invention comprises the conductive core, wherein the outer portion of the conductive core is bound to a plurality of ligands of the invention.

In some embodiments, ligands 16 are assembled to form a shell on top of core 12. In some embodiments, ligands 16 are selected to make nanoparticle 10 characterized by sensitivity to the analyte of interest, wherein the analyte of interest is as described herein. In some embodiments, ligands 16 are selected to make nanoparticle 10 characterized by binding affinity for the analyte of interest, wherein the analyte of interest is as described herein. Therefore, each ligand 16 comprises a first moiety thereof capable of binding to the core and a second moiety covalently bound to said first moiety, such that the second moiety is an alkyl-aryl moiety comprising at least 2 aliphatic carbon atoms.

In some embodiments, the ligands are covalently bound to the outer portion (or outer surface) of the conductive core, to form a shell. In some embodiments, the ligands are bound to the conductive core via the first moiety (or via derivative thereof). In some embodiments, each ligand is bound to a metal atom of the conductive core via a covalent (including inter alia a coordinative bond) and/or a non-covalent bond (such as hydrogen bonds, electrostatic interactions, Van-der-Waals bonds, dipol-dipol interactions, etc.). In some embodiments, each ligand is stably complexed by the metal (e.g. the ligand forms a coordinative bond with the metal atom). In some embodiments, the ligands are chemisorbed and/or physisorbed to the conductive core. In some embodiments, the ligands are stably bound to the conductive core. In some embodiments, the term "stable" refers to the chemical stability (e.g. substantially devoid of bond cleavage) of the bond under ambient conditions (a temperature of less than 100° C., normal pressure or vacuum, and optionally ambient atmosphere), for a time period of between 1 day and 1 year including any range between.

In some embodiments, the ligands are bound to the outer portion of the conductive core, so as to form of a self-assembled monolayer (SAM). In some embodiments, the plurality of ligands are in a form of SAM on top the conductive core, thus forming a shell. In some embodiments, the shell is in a form of a layer. In some embodiments, the shell is in a form of a consecutive layer, optionally having a substantially uniform thickness. In some embodiments, the shell substantially encloses the conductive core.

In some embodiments, the shell is substantially devoid of a metal. In some embodiments, the shell is substantially devoid of an additional molecule other than the ligands. In some embodiments, the shell comprises trace level impurities such as an organic solvent and/or one or more impurities (e.g. aromatic and/or aliphatic molecules, and/or unbound ligands).

In some embodiments, the shell and/or the nanoparticle of the invention consists essentially of the conductive metal core and the ligands, as described herein. In some embodiments, at least 80%, at least 90%, at least 93%, at least 95%, at least 97%, at least 99.9%, or 100% by weight and/or volume of the shell consist of the ligands bound thereto, including any range between.

In some embodiments, at least 80%, at least 90%, at least 93%, at least 95%, at least 97%, at least 99.9%, or 100% including any range between, by weight of the nanoparticle consist of the conductive core and the ligands bound thereto.

In some embodiments, a weight ratio between the conductive core and the shell within the nanoparticle is between 20:1 and 2:1, between 20:1 and 15:1, between 15:1 and 10:1, between 10:1 and 3:1, between 10:1 and 8:1, between 8:1 and 5:1, between 5:1 and 3:1, between 5:1 and 2:1, including any range between.

In some embodiments, the nanoparticle is characterized by resistivity of less than 100 $\Omega$cm, less than 10 $\Omega$cm less than $10^{-}\Omega$cm, less than $10^{-2}$ $\Omega$cm, less than $10^{-3}$ $\Omega$cm, less than $10^{-4}$ $\Omega$cm, less than $10^{-5}$ $\Omega$cm, less than $10^{-8}$ $\Omega$cm, less than $10^{-10}$ $\Omega$cm, including any range between, when measured at 20° C. In some embodiments, the nanoparticle is characterized by resistivity between 100 and $10^{-3}$ $\Omega$cm, between 100 and 10 $\Omega$cm, between 10 and 1 $\Omega$cm, between 1 and $10^4$ $\Omega$cm, between 0.1 and $10^{-3}$ $\Omega$cm, including any range between. In some embodiments, the resistivity of the nanoparticles refers to the resistivity of the sensing element of the invention.

Ligands

In some embodiments, each ligand independently comprises a first moiety covalently bound to an alkyl-aryl moiety, wherein the first moiety is capable of binding to the conductive core (e.g. via a covalent bond). In some embodiments, the first moiety is capable of forming a complex with the metal atom. In some embodiments, the first moiety is capable of forming a covalent bond to a reactive group on the outer portion of the conductive core. In some embodiments, the conductive core is or comprises a metal oxide and/or a metal in an elemental state; and wherein the outer portion of the conductive core comprises a plurality of hydroxy groups. In some embodiments, the first moiety (such as carboxy, alkylsilyl, or halosilyl) is capable of forming a covalent bond to a hydroxy group at the outer portion of the conductive core.

In some embodiments, the first moiety has a binding affinity for a metal atom. In some embodiments, the first moiety (e.g. a thiol) has reactivity to a metal atom (e.g. wherein a metal atom is in an elemental state). In some embodiments, the first moiety is capable of forming an electrostatic interaction, a covalent bond, a coordinative bond including any combination thereof, with metal atom at the outer portion of the nanoparticle. In some embodiments, the first moiety is a thiol and is capable of undergo a reaction with a metal atom (e.g. Au, Pt), to obtain a thiol-metal complex.

In some embodiments, the first moiety comprises thio, carboxy, carbonyl, amino, hydroxy, amide, optionally substituted disulfide, silyl, diazo, heteroaryl, an olefin, phosphate, silyl, phosphine, including any salt, any derivative or any combination thereof.

Other functional group capable of reacting with the metal atom, or with the reactive group as described herein, to coordinatively bind the metal or to form a covalent bond with the reactive group, respectively, are well-known in the art.

In some embodiments, the ligand of the invention is bound to the metal atom and/or to a reactive group on the outer portion of the conductive core, via a derivative of the first moiety. In some embodiments, a derivative of the first moiety includes any chemical modification and/or a salt thereof.

One of ordinary skills in the art will appreciate, that upon covalent bond formation the first moiety may undergo for example deprotonation and/or loss of a leaving group (e.g. hydroxy group, or halo group in the case of a condensation reaction), being referred to as a "derivative of the first moiety".

In some embodiments, the alkyl-aryl moiety comprises one or more alkyl chains bound to an aryl (e.g. an aromatic ring, a heteroaromatic ring, and/or mixed polycyclic aryl), wherein the alkyl-aryl moiety comprises at least two aliphatic carbon atoms. In some embodiments, the alkyl-aryl moiety is bound to the first moiety via a carbon atom of the alkyl chain. In some embodiments, the alkyl-aryl moiety comprises a plurality (e.g. 2, 3, or 4) of alkyl chains. In some embodiments, each of the alkyl chain(s) is optionally substituted and optionally comprises a heteroatom and/or an unsaturated bond (e.g. an alkenyl group). In some embodiments, each of the alkyl chain(s) comprises at least two carbon atoms. In some embodiments, the alkyl chains are bound to the aryl in meta-, or in para-position.

As used herein, the term "alkyl" also encompasses an alkenyl and/or alkynyl.

In some embodiments, the alkyl-aryl moiety comprises two alkyl chains bound to the aryl.

In some embodiments, the ligand is represented by Formula 1:

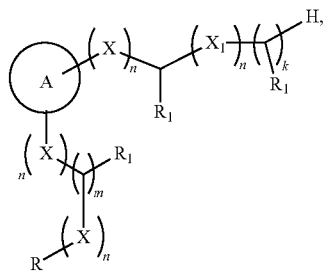

wherein:
R represents the first moiety (or a derivative thereof), wherein the first moiety is as described herein;
each R1 independently represents a substituent or H;
each X and X1 independently represents a heteroatom, —CHR1-, —C(R1)$_2$—, or is absent;
A represents an optionally substituted aryl, an optionally substituted heteroaryl, a polycyclic aryl, or any combination thereof;
n and k are integers each independently ranging from 0 to 5; and
m is an integer ranging from 1 to 5; and wherein the substituent comprises one or more of: C1-C6 alkyl, halo, NO$_2$, CN, OH, NH$_2$, carbonyl, CONH$_2$, CONR'$_2$, CNNR$_2$, CSNR$_2$, CONH—OH, CONN—NH$_2$, NHCOR', NHCSR', NHCNR', —NC(=O)OR', —NC(=O)NR', —NC(=S)OR', —NC(=S)NR', SO$_2$R', SOR', —SR', SO$_2$OR', SO$_2$N(R')$_2$, —NHNR'$_2$, —NNR', NH(C1-C6 alkyl), N(C1-C6 alkyl)$_2$, C1-C6 alkoxy, C1-C6 haloalkoxy, hydroxy(C1-C6 alkyl), hydroxy(C1-C6 alkoxy), alkoxy(C1-C6 alkyl), alkoxy(C1-C6 alkoxy), amino(C1-C6 alkyl), CONH(C1-C6 alkyl), CON(C1-C6 alkyl)$_2$, CO$_2$H, CO$_2$R', —OCOR', —OCOR', —OC(=O)OR', —OC(=O)NR', —OC(=S)OR', —OC(=S)NR', a heteroatom, an optionally substituted cycloalkyl, an optionally substituted heterocyclyl, or a combination thereof, wherein each R' is independently selected from hydrogen, alkyl, cycloalkyl, alkenyl, aryl, heteroaryl (e.g. optionally bonded through a ring carbon, or through a heteroatom) or heterocyclyl (e.g. optionally bonded through a ring carbon, or through a heteroatom). In some embodiments, the ligand is represented by Formula 1, including any salt and/or any tautomer thereof.

In some embodiments, the term "polycyclic aryl" encompasses a plurality (e.g. 2, 3, 4, 5 or 6) of fused or adjacent rings (e.g. biaryl); wherein at least one ring is an aryl (also including heteroaryl), and any additional ring is independently selected from aryl, heteroaryl, an optionally unsaturated cycloalkyl, an optionally unsaturated heterocyclyl, or any combination thereof, and wherein each ring is optionally substituted. In some embodiments, the term "polycyclyl" encompasses a polycyclic aromatic ring, a polycyclic aliphatic ring, or a mixed polycyclic aryl.

In some embodiments, the term "mixed polycyclic aryl" refers to any plurality of rings covalently bound to each other (e.g. fused rings, dicylyls, spirocyclic rings etc.) comprising at least one aromatic ring (aryl, or heteroaryl) and at least one aliphatic or non-aromatic ring (optionally a heterocyclyl and/or unsaturated cyclyl).

In some embodiments, the term "substituted" comprises more or more (e.g. 2, 3, 4, 5, 6, or more) substituents, wherein the substituent(s) is as described herein.

In some embodiments, n and k are integers each independently ranging from 0 to 5, from 0 to 1, from 1 to 5, from 1 to 3, from 3 to 5, including any range between. In some embodiments, if X1 is a heteroatom, then k is not 0 (e.g. ranges between 1 and 5, or k is any of 1, 2, 3, 4, or 5). In some embodiments, if X1 is a heteroatom, then k is 1.

In some embodiments, m ranges from 1 to 5, from 1 to 3, from 3 to 5, including any range between. In some embodiments, m is between 1 and 3. In some embodiments, m is 2.

In some embodiments, the alkyl-aryl moiety is represented by Formula 2:

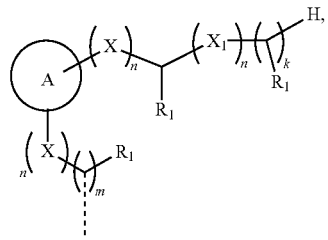

wherein R1, X, X1, A, m, n, and k are as described herein, and wherein the dashed line represents an attachment point to the first moiety.

In some embodiments, each R1 independently represents a substituent or H, wherein the substituent is as described herein. In some embodiments, each X and X1 independently represents a heteroatom, or is absent. In some embodiments, A represents an optionally substituted aryl, an optionally substituted heteroaryl, or both.

In some embodiments, the heteroatom is selected from the group consisting of O, S, NH, NR1, PH and PR1 or a combination thereof; wherein R1 is as described herein. In some embodiments, the heteroatom is O, NR1 or S.

In some embodiments, the alkyl-aryl moiety is represented by Formula 2A:

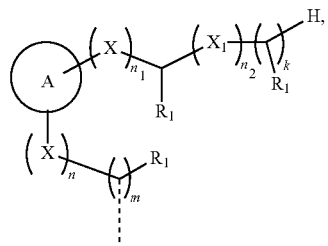

wherein R1, A, m, n, and k are as described herein, and the dashed line represents an attachment point to the first moiety; X, X1, each independently represents a heteroatom, as described herein; and wherein n1, n2 each independently represent an integer between 0 and 3, between 0 and 1, between 1 and 3, including any range between. In some embodiments, if n2 is not 0, then k is 1. In some embodiments, n1 and n2 are 0, and k is at least 1. In some embodiments, n1 and n2 each independently is 0 or 1. In some embodiments, the sum of the numerical values of n1, n2 and k is at least 1. In some embodiments, the sum of the numerical values of n1, n2 and k is between 1 and 3. In some embodiments, the sum of the numerical values of n1, n2 and k is 1 or 2.

In some embodiments, the alkyl chains are bound to A in meta-, or in para-position to each other.

In some embodiments, n is 1 or 0, and if n is 1 then m is between 1 and 2. In some embodiments, n is 0, and m is 1, 2 or 3. In some embodiments, the sum of the numerical values of n and m is 2 or 3.

In some embodiments, n1 and/or n2 are 0 and k is 1 to 3. In some embodiments, n is 0, and m is 1, 2 or 3. In some embodiments, n1 and n2 are both 0, and k is at least 1. In some embodiments, n1 and n2 are both 0 and k is 1, 2, or 3. In some embodiments, n1 and n2 are both 0 and k is 2.

In some embodiments, the first moiety (or a derivative thereof) comprises thio, carboxy, carbonyl, amino, hydroxy, silyl, alkoxysilyl, hydroxysilyl, halosilyl, diazo, amide, optionally substituted disulfide, heteroaryl, an olefin, phosphate, silyl, phosphine, including any salts, any derivative or any combination thereof. In some embodiments, the first moiety (or a derivative thereof) is or comprises thio, carboxy, ester, silyl, a silanol (including diols and triols), or any combination thereof.

In some embodiments, m and k each independently is 1 or 2.

In some embodiments, the alkyl-aryl moiety is represented by Formula 3:

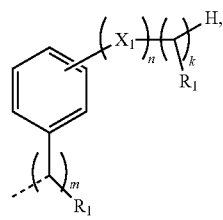

wherein X1, R1 and n are as described herein, and m is at least 2, and wherein k is between 1 and 5, or between 2 and 5. In some embodiments, the alkyl-aryl moiety is represented by Formula 3, wherein k is at least 2. In some embodiments, the alkyl-aryl moiety is represented by Formula 3, wherein n is 0 and k is 1, 2, or 3. In some embodiments, the alkyl-aryl moiety is represented by Formula 3, and the alkyl chains are bound to the phenyl ring in meta- or para-position.

In some embodiments, the alkyl-aryl moiety is represented by any of Formulae 1-3, wherein R1 is hydrogen. In some embodiments, the alkyl-aryl moiety is represented by any of Formulae 1-3, wherein R1 is hydrogen and each of n, n1, and n2 is 0.

In some embodiments, the first moiety is or comprises thiol or thiolate.

In some embodiments, the nanoparticle of the invention comprises a single ligand species. In some embodiments, the nanoparticle of the invention comprises a plurality (e.g. 2, 3, 4, 5, 6 or 10 including any range between) of different ligand species.

In some embodiments, the ligand is or comprises:

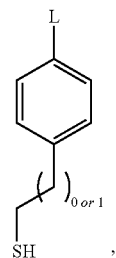

wherein L is any of:

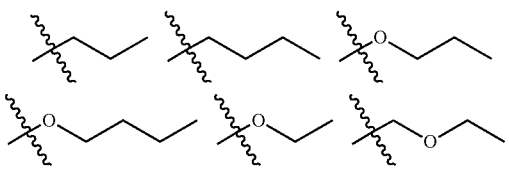

In some embodiments, the ligand is or comprises:

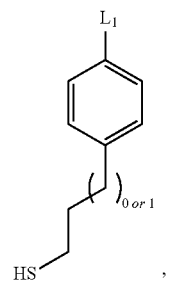

wherein L1 is any of:

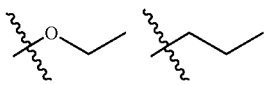

In some embodiments, the ligand is or comprises at least one of:

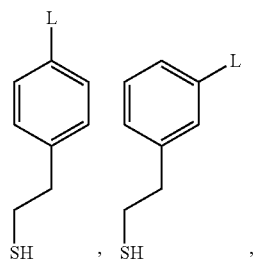

wherein L comprises ethyl or butyl.

In some embodiments, the alkyl comprises a C1-C10 alkyl. In some embodiments, C1-C10 alkyl is a branched or a linear alkyl (optionally substituted), and comprising between 1 and 10, between 1 and 5, between 1 and 2, between 2 and 4, between 4 and 6, between 6 and 8, between 8 and 10, carbon atoms, including any range or value therebetween. In some embodiments, the alkyl comprises a C1-C6 alkyl. In some embodiments, C1-C10 alkyl is a branched or a linear alkyl (optionally substituted), and comprising between 1 and 6, between 1 and 5, between 1 and 2, between 2 and 4, between 4 and 6, between 2 and 6, between 1 and 3, between 3 and 6, between 1 and 4, between 3 and 5, between 5 and 6, carbon atoms, including any range or value therebetween.

In some embodiments, the nanoparticle of the invention is characterized by sensitivity to the analyte of interest, wherein sensitivity is as described herein. In some embodiments, the nanoparticle of the invention is characterized by enhanced binding affinity for the analyte of interest, as compared to a control. In some embodiments, the binding affinity of the nanoparticle for the analyte of interest is enhanced by at least 2 times, at least 10 times, at least 100 times, at least 1000 times, at least 10.000 times, at least 1000.000 times, including any range between, as compared to a binding affinity for a control. In some embodiments, the nanoparticle of the invention is characterized by enhanced binding affinity for the analyte of interest, as compared to a control, wherein a concentration of the analyte of interest and of the control within the sample is substantially the same (e.g. less than 1000 ppm, less than 100 ppm, less than 10 ppm, less than 1 ppm, or between 1 ppb and 1 ppm, including any range between.

In some embodiments, the term "enhanced binding affinity" refers to an affinity ratio between (i) the binding affinity of the nanoparticle for the analyte of interest and (ii) the binding affinity of the nanoparticle for the control. In some embodiments, the enhanced binding affinity refers to an enhanced change in the electrical resistance of the nanoparticle upon exposure to the analyte of interest, as compared to the control. The binding affinity for a specific analyte may be deduced from the response intensity of a sensor (e.g. the sensor of the invention) upon exposure thereof to the specific analyte, wherein the sensor comprises the nanoparticles of the invention within the sensing element. For example, an enhanced binding affinity of the nanoparticle for a specific analyte will result in an enhanced response of the sensor. Thus, the affinity ratio of the nanoparticle, predetermines the selectivity and/or sensitivity of the sensor of the invention.

In some embodiments, the term "response" refers to a signal generated by the sensor in response to the conductivity change of the sensing unit.

In some embodiments, the control refers to any gas (e.g. a VC such as $N_2$, $CO_2$, water) and/or a VOC other than the analyte of interest. In some embodiments, the control comprises, but is not limited to: isoprene, ketones (e.g. acetone), alcohols (e.g. methanol and/or ethanol), and water or any combination thereof. In some embodiments, a concentration of the control within a given gaseous sample is substantially the same or higher as the concentration of the analyte of interest. For example: a concentration of acetone within a gaseous sample may be between 300 and 800 ppb, a concentration of isoprene within a gaseous sample may be between about 100 ppb, a concentration of water within a gaseous sample may be about 1% (or 10,000 ppm), a concentration of an aldehyde (an exemplary analyte of interest) within a gaseous sample may be between about 3 to 100 ppb, including any range between.

In some embodiments, the control refers to a VOC (e.g. an organic molecule having a chemical structure similar to the analyte of interest). In some embodiments, the control refers to a VOC present within a gaseous sample at a similar concertation range as the analyte of interest (e.g. between 1 ppb and 1 ppm).

In another aspect, there is provided a chemiresistor sensor comprising:
at least two electrodes; and at least one sensing element electrically connected to the two electrodes and comprising a structure made from a plurality of nanoparticles of the invention, and wherein the chemiresistor sensor is configured to detect one or more analyte (s) of interest in a gaseous sample.

In some embodiments, the sensor is configured to detect the presence of the analyte of interest and the concentration thereof in a gaseous sample. In some embodiments, the gaseous sample comprises the analyte of interest and the control. In some embodiments, the analyte of interest is a VOC.

As used herein, the term VOC refers to organic small molecules (usually having a molecular weight less than 1000 Da, or less than 500 Da) characterized by high vapor pressure (e.g. at least $10^{-10}$ atm) at room temperature.

In some embodiments, the analyte of interest is selected from or comprises an aldehyde, an alkane, or a combination thereof.

In some embodiments, the plurality of nanoparticles of the invention comprise substantially the same particles. In some embodiments, at least 80%, at least 90%, at least 95%, at least 97%, at least 99%, including any range between, by total weight of the nanoparticles are chemically identical particles.

In some embodiments, at least a portion of the plurality of nanoparticles of the invention are chemically distinct particles (e.g. having chemically identical cores and chemically distinct ligand specie(s) bound thereto, or having chemically identical ligands and chemically distinct cores). In some embodiments, the sensor comprises a plurality (e.g. 2, 3, 4, 5, 6 or 10 including any range between) of chemically distinct particles.

In some embodiments, each of the nanoparticles of the invention comprises the same conductive core, and the same or different ligand species. In some embodiments, at least a portion of the nanoparticles of the invention have chemically distinct conductive cores and the same or different ligand species.

In some embodiments, the average cross section size of the conductive core of the plurality of nanoparticles is between 1 and 100 nm, between 1 and 10 nm, between 10 and 50 nm, between 50 and 100 nm, including any range between. In some embodiments, the average cross section size of the conductive core is between 1 and 20 nm, between 1 and 10 nm, between 10 and 15 nm, between 15 and 20 nm, between 1 and 5 nm, between 1 and 3 nm, between 3 and 5 nm, between 5 and 7 nm, between 7 and 10 nm, including any range between.

In some embodiments, the plurality of nanoparticles of the invention is characterized by a particle size in a range between 1 and 100 nm, between 1 and 10 nm, between 10 and 50 nm, between 50 and 100 nm, including any range between. In some embodiments, the nanoparticles of the invention are characterized by a particle size in a range between 1 and 5 nm, between 1 and 3 nm, between 3 and 5 nm, between 5 and 7 nm, between 7 and 10 nm, including any range between. In some embodiments, the term "particle size" refers to average cross section size of the nanoparticles.

In some embodiments, the analyte of interest comprises any of: an aldehyde, an optionally unsaturated aliphatic aldehyde such as C1-C20, or C5-C20 aliphatic aldehyde, an optionally unsaturated alkane such as C1-C20, or C5-C20 alkane C6-C20 alkane C6-C10 alkane C5-C15 alkane. In some embodiments, the analyte of interest comprises a saturated alkane, optionally substituted by one or more substituents. In some embodiments, the saturated alkane comprises at least 2, at least 3, at least 4, at least 6, carbon atoms. In some embodiments, the saturated alkane comprises between C5-C20 C6-C20 C6-C10 and C5-C15 carbon atoms, including any range between.

In some embodiments, the analyte of interest comprises an aldehyde, wherein the aldehyde comprises a hydrocarbon chain comprising between 1 and 20 carbon atoms. In some embodiments, the aldehyde is an aliphatic aldehyde comprising at least 2, at least 3, at least 4, at least 6, or at least 5 carbon atoms. In some embodiments, the aldehyde is (C1-C20)-C(=O)—H.

In some embodiments, the nanoparticle(s) of the invention and/or the chemiresistor sensor comprising thereof, is characterized by an enhanced sensitivity to the gaseous analyte of interest, as compared to a control (e.g. a VOC such as a conjugated alkene (e.g. isoprene or any structurally related compound), a ketone (e.g. acetone), an alcohol and/or a VC such as N2, CO2, water, etc.), wherein the analyte of interest and the control are as described herein.

In some embodiments, the chemiresistor sensor is characterized by sensitivity and/or binding affinity to the analyte of interest, wherein sensitivity and binding affinity are as described herein.

In some embodiments, the sensitivity of the chemiresistor sensor to the analyte of interest is at least 10, at least 100, at least 1000, at least 10.000, at least 100.000, including any range between, as compared to the control. In some embodiments, the sensitivity of the chemiresistor sensor to the analyte of interest is enhanced by at least 5 times, at least 10 times, at least 100 times, at least 1000 times, at least 10.000 times, at least 100.000 times, including any range between, as compared to the control. As used herein the term "sensitivity" refers to the ratio between signal intensities of the sensor in response to the analyte of interest and in response to the control (e.g. being referred to as 1), wherein the control and the analyte of interest are present within the sample.

Accordingly, the term "enhanced" when referring to sensitivity relates to the signal enhancement in response to the analyte of interest, relative to the response of the sensor to the control (wherein the signal intensity in response to the control is optionally referred to as 1). In some embodiments, one or analyte of interest and the control are present within the sample at the same concentration range (e.g. at ppb and/or ppm range). In some embodiments, the term "sensitivity" refers to a sample comprising a concentration of the control and of the analyte of interest ranging between 1 ppb and 1 ppm, including any range between. In some embodiments, the sensitivity of the sensor is predetermined by the affinity ratio of the nanoparticle of the invention. In some embodiments, the sensor is characterized by a detection limit of at least 1 ppb.

In some embodiments, the sensor is configured to selectively detect the analyte of interest within the sample. In some embodiments, the sensor is configured to selectively detect the analyte of interest, wherein a concentration of the analyte of interest within the sample is between 1 ppb and 1 ppm, including any range between.

In some embodiments, the sensor may be included in an array of sensing elements configured to detect the presence and/or concentration of an analyte of interest, for example, an aldehyde and/or an alkane, as described herein.

Method

In another aspect, there is provided a method for detection of an analyte of interest in a gaseous sample, comprising:
a. exposing the sensor of the invention to the gaseous sample;
b. providing electricity to the sensor, so as to obtain a plurality of conductivity values generated by the sensor; and
c. analyzing the resistivity values, thereby determining the presence and level of intensity (or concentration) of the analyte of interest within s the gaseous aid sample, wherein the analyte of interest comprises an aldehyde. In some embodiments, the aldehyde is as described hereinabove. In some embodiments, the analyte of interest comprises a plurality of aldehydes.

In some embodiments, providing electricity may include, measuring at least one of, the conductivity, resistivity, capacity, impedance, current and voltage of the sensor, when the sensor id exposed to VOCs.

Upon expositing the sensor to the presence of analyte, the resistivity of the sensing element changes. In some embodiments, measuring values related to the resistivity, conductivity, capacity and/or impedance of the at least one sensing element between the two electrodes, prior, during and after the exposure to the analyte is indicative to the amount and/or type of analyte attached/engaged with the sensing element. In some embodiments, the measured values are selected from: a temporal resistance, temporal conductivity, base resistance (e.g., background resistance), base conductivity, electrical noise, base current, based voltage, base frequency and base amplitude.

In some embodiments, the measured values may further be analyzed and manipulated (by a processor associated with the chemiresistor sensor) in order to further extract additional values. In some embodiments, the extracted values are selected from: the maximal subtracted resistance, the difference between maximum and minimum values, the average value, the maximum value, the minimum value, the first time derivative, the second time derivative, signal to noise ratio, incline gradient, decline gradient, rise time, overshooting value relative to steady state value, oscillation decay in time and oscillation frequency.

In some embodiments, the measured values and/or the extracted values may be used for detecting the presence and/or amount of a specific analyte, for example, aldehydes. In some embodiments, the measured values and/or the extracted values may be compared to a prestored data, for example, using any mathematical correlation and/or a calibration curve. In some embodiments, the mathematical correlation is one of: a linear correlation, a parabolic correlation, a polynomial correlation, logarithmic correlation, exponential correlation and power correlation.

In some embodiments, the sample comprises a plurality of gaseous analytes. In some embodiments, the sample comprises a plurality of VOCs. In some embodiments, the sample comprises one or more analytes of interest (e.g. an aldehyde, an optionally unsaturated aliphatic aldehyde such as C1-C20, or C5-C20 aliphatic aldehyde, an optionally unsaturated alkane such as C1-C20, C6-C20 alkane or C5-C20 alkane, or any combination thereof) and at least one additional gaseous species selected from alkene, alcohol, water and ketone or any combination thereof. In some embodiments, the sample further comprises one or more atmospheric gases (e.g. N2, O2, CO2, and/or water). In some embodiments, the sample has a temperature between −10 and 100° C., between −10 and 50° C., between 0 and 30° C., between 0 and 40° C., between 50 and 100° C., including any range between.

In some embodiments, the method is for selectively detecting the presence of the analyte of interest within the sample, wherein a concentration of the analyte within the sample is at least 1 ppb, at least 10 ppb, at least 50 ppb, at least 100 ppb, at least 500 ppb, including any range between.

In some embodiments, the gaseous sample comprises the analyte of interest at a concentration between 1 and 500 ppb, or between 1 ppb and 1 ppm; and a concentration of the additional species is at most 10 ppm, at most 1 ppm, at most 500 ppb, at most 100 ppb, and wherein the additional species is as described herein.

In some embodiments, exposing step is performed under operable conditions. In some embodiments, operable conditions comprise (i) a contacting time of at least 1 second (s), at least 2 s, at least 5 s, at least 8 s, at least 10 s, at least 30 s, at least 60 s, at least 1.5 minute (min), at least 2 min, at least 3 min, at least 5 min, or between 10 s and 10 min, between 10 s and 60 s, between 1 and 2 min, between 1 and 10 min, between 2 and 5 min, between 5 and 10 min, including any range between; and (ii) an operable temperature between −10 and 100° C., between 0 and 10° C., between 0 and 25° C., between 10 and 30° C., between 10 and 20° C., between 10 and 40° C., between 20 and 30° C., between 30 and 40° C., between 40 and 50° C., including any range between.

In some embodiments, operable conditions comprise a pressure between 0.5 and 2 bar, a relative humidity of between 0 and 100%, between 10 and 100%, between 0 and 10%, between 10 and 30%, between 30 and 100%, between 40 and 100%, between 40 and 60%, between 40 and 70%, between 40 and 80%, between 60 and 80%, between 80 and 100%, including any range between.

In some embodiments, exposing comprises contacting the chemiresistor sensor with a flowing gaseous sample. In some embodiments, the flowing gaseous sample is characterized by a flow rate between 50 and 2000 ml/min, between 50 and 100 ml/min, between 100 and 200 ml/min, between 100 and 2000 ml/min, between 200 and 1000 ml/min, between 200 and 500 ml/min, between 500 and 2000 ml/min, between 500 and 1000 ml/min, between 1000 and 2000 ml/min, including any range between.

Figure 4:
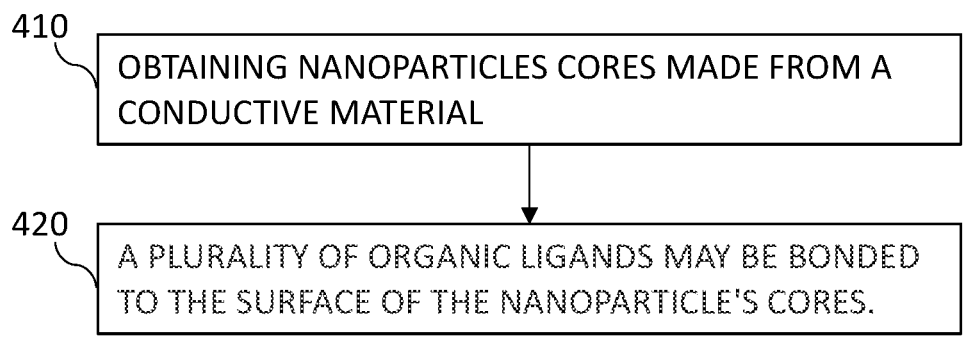
FIG. 4 is a flowchart of a method of making particles for chemiresistor sensor according to some embodiments of the invention.

Reference is now made to FIG. 4 which is a flowchart of a method of making particles for chemiresistor sensor according to some embodiments of the invention. In step 410, conductive cores 12 made from a conductive material, as listed herein above, may be obtained. In some embodiments, the conductive cores may be commercially available for purchasing, either as crystalline, amorphous and/or as an alloy. In some embodiments, the conductive cores may be prepared by well-known synthetic procedures, such as a co-dispersion, and/or by ball milling and the like.

In a non-limiting example, dry powder core nanoparticles are mixed with a solvent and any of the organic ligands, according to embodiments of the invention, at predetermined temperatures (e.g. 10° C., 20° C., 30° C. and 40° C.). The mixture can be stirred together for a period of time (e.g. 0.5-2 hours). In some embodiments, the solvent may be selected from the group consisting of sodium acetate, sodium borohydride or hydrazine, or any other suitable solvent. In some embodiments, to separate the dry core nanoparticles, sonication, ultrasonic method, homogenization agitation method (e.g., using a blade), and the like may be used.

In some embodiments, the conductive core particles may be prepared by reduction of a salt of the required metal(s), e.g. RuCF.xFhO or similar, by the use of a suitable reducing agent such as sodium acetate, sodium or other borohydride, hydrazine, or any available known reducing agent the materials may be held in aqueous solution and heated under reflux conditions or hydrothermal conditions, or by heating by microwave or other direct radiation. In these examples, depending on the process chosen, the metal salt and the reducing agent can be pre-mixed or mixed after heating to a desired temperature. Blending of the reducing agent with the metal salt, possibly with additional treatment such as heating/cooling, may lead to the formation of nucleated metal clusters that develop with time into nanoparticles in the reaction mixture. The growth of these particles may be controlled by one or more of: the type of ligands, reaction time, temperature, and in some cases the presence of surface-active agents (surfactants) or other additives to moderate growth of the particles.

In some embodiments, the rate of the reaction and the temperature may be determined for obtaining a crystalline or amorphous structure. For example, using slow rate (e.g., reducing agent insertion to the reaction) and higher temperature (e.g., 0-25° C.) may result in amorphous structure, while using higher reaction rate and lower temperature (e.g., lower than 0° C.) may result in crystalline structure.

In some embodiments, a conductive core having at least two types of materials may be prepared in a single step where salts of both materials are present in the reaction mixture. Such a one-step process (e.g., mixing the salts of different metals together) could lead either to alloys of the various particles, separate particles of each or some of the species, or a mixture thereof.

In step 420, the plurality of ligands 16 may be bonded (e.g., covalently bonded) with the surface of the core nanoparticles. For example, dry powder core nanoparticles may be mixed with solvents and ligands according to any of the embodiments disclosed herein above, and stirred together for a predetermined amount of time (e.g., a time period in the range of 0.5-2 hours) at a predetermined temperature (e.g., a temperature in the range of 10-40° C.). In some embodiments, the solvent may be selected from a group consisting of: sodium acetate, sodium borohydride or hydrazine, or any other suitable solvent. In some embodiments, in order to disperse the dry core nanoparticles, methods such as, sonication, ultrasonic methods, homogenizing stirring method (e.g., using blades) and the like may be applied.

In some embodiments, the synthesized nanoparticles are dispersed in solvent mixture (e.g., toluene, ethanol, acetone, other—ketones, alcohols, aromatic, or the like) to from stable ink, or possibly paste depending on printing method. The printing methods may be selected from: inkjet, die coating, screen printing, Dr, blade printing, or any other three-dimensional deposition method.

In some embodiments, ink is applied (by printer) to form the sensing element (e.g., sensing element 130) at a specific pattern on the surface of the electrode. Nonlimiting example for the size of such sensing element are, 1 mm×1 mm and a thickness of between 100 nm to 1000 nm. In some embodiments, the thickness is smaller than 1000 nm. In some embodiments, the thickness is smaller than 500 nm. In some embodiments, the thickness is smaller than 400 nm. In some embodiments, the thickness is smaller than 200 nm. In some embodiments, the thickness is smaller than 100 nm. At the end of the deposition/printing process solvents residues are extracted from the sensing element by natural evaporation or heat application (oven, light, UV, other), or vacuum application or combination (possibly in the printer).

General

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

As used herein, the term "substantially" refers to at least 80%, at least 85%, at least 90%, at least 92%, at least 95%, at least 96%, at least 97%, at least 98%, at least 99%, including any range or value therebetween. Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and/or engineering arts.

Further, all numerical values, e.g. when referring the amounts or ranges of the elements constituting the formulation are approximations which are varied (+) or (−) by up to 20%, at times by up to 10% of from the stated values. It is to be understood, even if not always explicitly stated that all numerical designations are preceded by the term "about".

The term "consisting essentially of" is used to define formulations which include the recited elements but exclude other elements that may have an essential significance on the formulation. "Consisting of" shall thus mean excluding more than trace elements of other elements. Embodiments defined by each of these transition terms are within the scope of this invention.

The term "substituent", as used herein comprises one or more substituents (e.g. 1, 2, 3, 4, 5, or 6), each independently selected from the group consisting of: C1-C6 alkyl, halo, —NO$_2$, —CN, —OH, —NH$_2$, carbonyl, —CONH$_2$, —CONR'$_2$, —CNNR$_2$, —CSNR$_2$, —CONH—OH, —CONH—NH$_2$, —NHCOR', —NHCSR', —NHCNR', —NC(=O)OR', —NC(=O)NR', —NC(=S)OR', —NC(=S)NR', —SO$_2$R', —SOR', —SR', —SO$_2$OR', —SO$_2$N(R')$_2$, —NHNR'$_2$, —NNR', —NH($C_1$-$C_6$ alkyl), —N($C_1$-$C_6$ alkyl)$_2$, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), amino($C_1$-$C_6$ alkyl), —CONH($C_1$-$C_6$ alkyl), —CON($C_1$-$C_6$ alkyl)$_2$, —CO$_2$H, —CO$_2$R', —OCOR', —OCOR', —OC(=O)OR', —OC(=O)NR', —OC(=S)OR', —OC(=S)NR', a heteroatom, an optionally substituted cycloalkyl, an optionally substituted heterocyclyl, or a combination thereof, wherein each R' is independently selected from hydrogen, alkyl, cycloalkyl, alkenyl, aryl, heteroaryl (e.g. optionally bonded through a ring carbon, or through a heteroatom) or heterocyclyl (e.g. optionally bonded through a ring carbon, or through a heteroatom).

As used herein, the term "alkyl" describes an aliphatic hydrocarbon including straight chain and branched chain groups. In some embodiments, the alkyl group has 1 to 20 carbon atoms, between 1 and 10, between 1 and 5, between 5 and 10, between 10 and 15, between 15 and 20, including any range between.

In some embodiments, the alkyl encompasses a short alkyl and/or a long alkyl. In some embodiments, the alkyl has from 21 to 100 carbon atoms, or more. In the context of the present invention, a "long alkyl" is an alkyl having at least 20 carbon atoms in its main chain (the longest path of continuous covalently attached atoms). A short alkyl therefore has 20 or less (e.g. 2, 3, 4, 5, 6, 8, 10, 15, or 20) main-chain carbons. The alkyl can be substituted or unsubstituted, as defined herein.

The term "alkyl", as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "cycloalkyl" describes an all-carbon monocyclic or fused ring (i.e. rings which share an adjacent pair of carbon atoms) group where one or more of the rings does not have a completely conjugated pi-electron system. The cycloalkyl group may be substituted or unsubstituted, as indicated herein.

The term "aryl" describes an all-carbon monocyclic or fused-ring polycyclic (i.e. rings which share adjacent pairs of carbon atoms) groups having a completely conjugated pi-electron system. The aryl group may be substituted or unsubstituted, as indicated herein.

The term "alkoxy" describes both an O-alkyl and an —O-cycloalkyl group, as defined herein. The term "aryloxy" describes an —O-aryl, as defined herein.

Each of the alkyl, cycloalkyl and aryl groups in the general formulas herein may be substituted by one or more substituents, whereby each substituent group can independently be, for example, halide, alkyl, alkoxy, cycloalkyl, nitro, amino, hydroxyl, thiol, thioalkoxy, carboxy, amide, aryl and aryloxy, depending on the substituted group and its position in the molecule. Additional substituents are also contemplated.

The term "halide", "halogen" or "halo" describes fluorine, chlorine, bromine or iodine. The term "haloalkyl" describes an alkyl group as defined herein, further substituted by one or more halide(s). The term "haloalkoxy" describes an alkoxy group as defined herein, further substituted by one or more halide(s). The term "hydroxyl" or "hydroxy" describes a —OH group. The term "mercapto" or "thiol" describes a —SH group. The term "thioalkoxy" describes both an —S-alkyl group, and a —S-cycloalkyl group, as defined herein. The term "thioaryloxy" describes both an —S-aryl and a —S-heteroaryl group, as defined herein. The term "amino" describes a —NR'R" group, or a salt thereof, with R' and R" as described herein.

The term "heterocyclyl" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofuran, tetrahydropyran, morpholino and the like.

The term "carboxy" describes a —C(O)OR' group, or a carboxylate salt thereof, where R' is hydrogen, alkyl, cycloalkyl, alkenyl, aryl, heteroaryl (e.g. optionally bonded through a ring carbon, or through a heteroatom) or heterocyclyl (e.g. optionally bonded through a ring carbon, or through a heteroatom) as defined herein.

In some embodiments, R' and R" are the same or different, wherein each of R' and R" is independently selected from hydrogen, alkyl, cycloalkyl, alkenyl, aryl, heteroaryl (e.g. optionally bonded through a ring carbon, or through a heteroatom) or heterocyclyl (e.g. optionally bonded through a ring carbon, or through a heteroatom) as defined herein.

The term "carbonyl" describes a —C(O)R' group, where R' is as defined hereinabove. The above-terms also encompass thio-derivatives thereof (thiocarboxy and thiocarbonyl).

The term "thiocarbonyl" describes a —C(S)R' group, where R' is as defined hereinabove. A "thiocarboxy" group describes a —C(S)OR' group, where R' is as defined herein. A "sulfinyl" group describes an —S(O)R' group, where R' is as defined herein. A "sulfonyl" or "sulfonate" group describes an —S(O)2R' group, where R' is as defined herein.

A "carbamyl" or "carbamate" group describes an —OC(O)NR'R" group, where R' is as defined herein and R" is as defined for R'. A "nitro" group refers to a —NO$_2$ group. The term "amide" as used herein encompasses C-amide and N-amide. The term "C-amide" describes a —C(O)NR'R" end group or a —C(O)NR'-linking group, as these phrases are defined hereinabove, where R' and R" are as defined herein. The term "N-amide" describes a —NR"C(O)R' end group or a —NR'C(O)— linking group, as these phrases are defined hereinabove, where R' and R" are as defined herein.

A "cyano" or "nitrile" group refers to a —CN group. The term "azo" or "diazo" describes an —N=NR' end group or an —N=N— linking group, as these phrases are defined hereinabove, with R' as defined hereinabove. The term "guanidine" describes a —R'NC(N)NR"R'" end group or a —R'NC(N) NR"— linking group, as these phrases are defined hereinabove, where R', R" and R'" are as defined herein. As used herein, the term "azide" refers to a —N3 group. The term "sulfonamide" refers to a —S(O)2NR'R" group, with R' and R" as defined herein.

The term "phosphonyl" or "phosphonate" describes an —OP(O)—(OR')2 group, with R' as defined hereinabove. The term "phosphinyl" describes a —PR'R" group, with R' and R" as defined hereinabove. The term "alkylaryl" describes an alkyl, as defined herein, which substituted by an aryl, as described herein. An exemplary alkylaryl is benzyl.

The term "heteroaryl" describes a monocyclic or fused ring (i.e. rings which share an adjacent pair of atoms) group having in the ring(s) one or more atoms, such as, for example, nitrogen, oxygen and sulfur and, in addition, having a completely conjugated pi-electron system. As used herein, the term "heteroaryl" refers to an aromatic ring in which at least one atom forming the aromatic ring is a heteroatom. Heteroaryl rings can be foamed by three, four, five, six, seven, eight, nine and more than nine atoms. Heteroaryl groups can be optionally substituted. Examples of heteroaryl groups include, but are not limited to, aromatic C3-8 heterocyclic groups containing one oxygen or sulfur atom, or two oxygen atoms, or two sulfur atoms or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl is selected from among oxazolyl, isoxazolyl, oxadiazolyl, thiazolyl, isothiazolyl, pyridinyl, pyridazinyl, pyrimidinal, pyrazinyl, indolyl, benzimidazolyl, quinolinyl, isoquinolinyl, quinazolinyl or quinoxalinyl.

In some embodiments, a heteroaryl group is selected from among pyrrolyl, furanyl (furyl), thiophenyl (thienyl), imidazolyl, pyrazolyl, 1,2,3-triazolyl, 1,2,4-triazolyl, 1,3-oxazolyl (oxazolyl), 1,2-oxazolyl (isoxazolyl), oxadiazolyl, 1,3-thiazolyl (thiazolyl), 1,2-thiazolyl (isothiazolyl), tetrazolyl, pyridinyl (pyridyl)pyridazinyl, pyrimidinyl, pyrazinyl, 1,2,3-triazinyl, 1,2,4-triazinyl, 1,3,5-triazinyl, 1,2,4,5-tetrazinyl, indazolyl, indolyl, benzothiophenyl, benzofuranyl, benzothiazolyl, benzimidazolyl, benzodioxolyl, acridinyl, quinolinyl, isoquinolinyl, quinazolinyl, quinoxalinyl, phthalazinyl, thienothiophenyl, 1,8-naphthyridinyl, other naphthyridinyls, pteridinyl or phenothiazinyl. Where the heteroaryl group includes more than one ring, each additional ring is the saturated form (perhydro form) or the partially unsaturated form (e.g., the dihydro form or tetrahydro form) or the maximally unsaturated (nonaromatic) form. The term heteroaryl thus includes bicyclic radicals in which the two rings are aromatic and bicyclic radicals in which only one ring is aromatic. Such examples of heteroaryl are include 3H-indolinyl, 2(1H)-quinolinonyl, 4-oxo-1,4-dihydroquinolinyl, 2H-1-oxoisoquinolyl, 1,2-dihydroquinolinyl, (2H)quinolinyl N-oxide, 3,4-dihydroquinolinyl, 1,2-dihydroisoquinolinyl, 3,4-dihydro-isoquinolinyl, chromonyl, 3,4-dihydroiso-quinoxalinyl, 4-(3H) quinazolinonyl, 4H-chromenyl, 4-chromanonyl, oxindolyl, 1,2,3,4-tetrahydroisoquinolinyl, 1,2,3,4-tetrahydro-quinolinyl, 1H-2,3-dihydroisoindolyl, 2,3-dihydrobenzo[f]isoindolyl, 1,2,3,4-tetrahydrobenzo-[g]isoquinolinyl, 1,2,3,4-tetrahydro-benzo[g]isoquinolinyl, chromanyl, isochromanonyl, 2,3-dihydrochromonyl, 1,4-benzo-dioxanyl, 1,2,3,4-tetrahydro-quinoxalinyl, 5,6-dihydro-quinolyl, 5,6-dihydroiso-quinolyl, 5,6-dihydroquinoxalinyl, 5,6-dihydroquinazolinyl, 4,5-dihydro-1H-benzimidazolyl, 4,5-dihydro-benzoxazolyl, 1,4-naphthoquinolyl, 5,6,7,8-tetrahydro-quinolinyl, 5,6,7,8-tetrahydro-isoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydro-benzoxazolyl, 1H-4-oxa-1,5-diaza-naphthalen-2-onyl, 1,3-dihydroimidizolo-[4,5]-pyridin-2-onyl, 2,3-dihydro-1,4-dinaphtho-quinonyl, 2,3-dihydro-1H-pyrrol[3,4-b]quinolinyl, 1,2,3,4-tetrahydrobenzo[b]-[1,7]naphthyridinyl, 1,2,3,4-tetra-hydrobenz[b][1,6]-naphthyridinyl, 1,2,3,4-tetrahydro-9H-pyrido[3,4-b]indolyl, 1,2,3,4-tetrahydro-9H-pyrido[4,3-b]indolyl, 2,3-dihydro-1H-pyrrolo-[3,4-b]indolyl, 1H-2,3,4,5-tetrahydro-azepino[3,4-b]indolyl, 1H-2,3,4,5-tetrahydroazepino-[4,3-b]indolyl, 1H-2,3,4,5-tetrahydro-azepino[4,5-b]indolyl, 5,6,7,8-tetrahydro[1,7]napthyridinyl, 1,2,3,4-tetrahydro-[2,7]-naphthyridyl, 2,3-dihydro[1,4]dioxino[2,3-b]pyridyl, 2,3-dihydro[1,4]-dioxino[2,3-b]pryidyl, 3,4-dihydro-2H-1-oxa[4,6]diazanaphthalenyl, 4,5,6,7-tetrahydro-3H-imidazo-[4,5-c]pyridyl, 6,7-dihydro[5,8]diazanaphthalenyl, 1,2,3,4-tetrahydro[1,5]-napthyridinyl, 1,2,3,4-tetrahydro[1,6]napthyridinyl, 1,2,3,4-tetrahydro[1,7]napthyridinyl, 1,2,3,4-tetrahydro-[1,8]napthyridinyl or 1,2,3,4-tetrahydro[2,6]napthyridinyl. In some embodiments, heteroaryl groups are optionally substituted. In one embodiment, the one or more substituents are each independently selected from among halo, hydroxy, amino, cyano, nitro, alkylamido, acyl, C1-6-alkyl, C1-6-haloalkyl, C1-6-hydroxyalkyl, C1-6-aminoalkyl, C1-6-alkylamino, alkylsulfenyl, alkylsulfinyl, alkylsulfonyl, sulfamoyl, or trifluoromethyl.

Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline and quinoxaline. In some embodiments, the substituents are halo, hydroxy, cyano, 0-C1-6-alkyl, C1-6-alkyl, hydroxy-C1-6-alkyl and amino-C1-6-alkyl.

As used herein, the terms "halo" and "halide", which are referred to herein interchangeably, describe an atom of a halogen, that is fluorine, chlorine, bromine or iodine, also referred to herein as fluoride, chloride, bromide and iodide.

Unless explicitly stated, the method embodiments described herein are not constrained to a particular order or sequence. Furthermore, all formulas described herein are intended as examples only and other or different formulas may be used. Additionally, some of the described method embodiments or elements thereof may occur or be performed at the same point in time.

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

Various embodiments have been presented. Each of these embodiments may of course include features from other embodiments presented, and embodiments not specifically described may include various features described herein.

The invention claimed is:

1. A nanoparticle, comprising a conductive core in contact with a plurality of ligands bound to said core, wherein:

each ligand comprises a first moiety thereof capable of binding to the core and a second moiety covalently bound to said first moiety;
wherein the second moiety is an alkyl-aryl moiety comprising at least 2 aliphatic carbon atoms
and the plurality of ligands are assembled to form a shell on top of said core;
and wherein said nanoparticle is characterized by sensitivity to an analyte of interest.

2. The nanoparticle of claim 1, wherein each of the plurality of ligands is bound to the core via the first moiety, and wherein said bound is via a covalent bond and wherein the covalent bond comprises a coordinative bond.

3. The nanoparticle of claim 1, wherein each core independently comprises a transitional metal, optionally wherein the transitional metal is substantially in an elemental state within said core.

4. The nanoparticle of claim 1, wherein the ligand is represented by Formula 1:

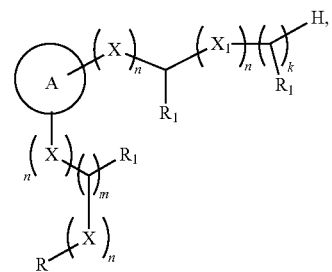

wherein:
R represents the first moiety;
each R1 independently represents a substituent or H;
each X and X1 independently represents a heteroatom, —CHR1-, —CR1R1-, or is absent;
A represents an optionally substituted aryl, an optionally substituted heteroaryl, a polycyclic aryl or any combination thereof;
n and k are integers each independently ranging from 0 to 5; and
m is an integer ranging from 1 to 5.

5. The nanoparticle of claim 4, wherein said heteroatom is selected from the group consisting of O, S, NH, NR1, PH and PR1 or a combination thereof; and if X1 represents the heteroatom then k ranges between 1 and 5.

6. The nanoparticle of claim 1, wherein the first moiety comprises thio, carboxy, carbonyl, amino, hydroxy, amide, optionally substituted disulfide, silyl, diazo, heteroaryl, an olefin, phosphate, silyl, phosphine, including any salts, any derivative or any combination thereof.

7. The nanoparticle of claim 1, wherein said first moiety comprises thio or thiolate, and wherein the alkyl-aryl moiety is represented by Formula 2:

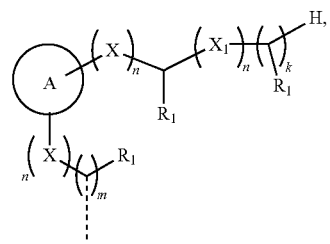

wherein:
each R1 independently represents a substituent or H;
each X and X1 independently represents a heteroatom, or is absent;
A represents an optionally substituted aryl, an optionally substituted heteroaryl, or any combination thereof the dashed line represents an attachment point to the first moiety;
the heteroatom is selected from the group consisting of O, S, NH, and NR1, or a combination thereof;
n is an integer each independently being 0 or 1;
k is an integer ranging from 0 to 5;
m is an integer ranging from 1 to 5; and if X1 represents the heteroatom then k ranges between 1 and 5.

8. The nanoparticle of claim 7, wherein m and k each independently is 1 or 2.

9. The nanoparticle of claim 1, wherein the alkyl-aryl moiety comprises an aryl substituted in meta-, or in para-position.

10. The nanoparticle of claim 1, wherein the alkyl-aryl moiety is represented by Formula 3:

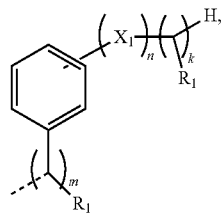

wherein m is 2, and wherein k is between 1 and 3.

11. The nanoparticle of claim 1, wherein the ligand comprises at least one of:

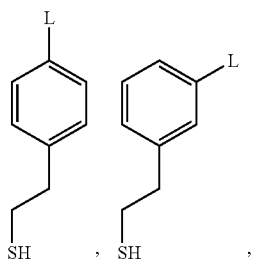

wherein L comprises ethyl or butyl.

12. The nanoparticle of claim 7, wherein said substituent comprises one or more substituents, each independently selected from the group consisting of: $C_1$-$C_6$ alkyl, halo, —$NO_2$, —CN, —OH, —$NH_2$, carbonyl, —$CONH_2$, —$CONR'_2$, —$CNNR_2$, —$CSNR_2$, —CONH—OH, —CONH—$NH_2$, —NHCOR', —NHCSR', —NHCNR', —NC(=O)OR', —NC(=O)NR', —NC(=S)OR', —NC(=S)NR', —$SO_2R'$, —SOR', —SR', —$SO_2OR'$, —$SO_2N(R')_2$, —$HNR'_2$, —NNR', —NH($C_1$-$C_6$ alkyl), —N($C_1$-$C_6$ alkyl)$_2$, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy ($C_1$-$C_6$ alkoxy), amino($C_1$-$C_6$ alkyl), —CONH($C_1$-$C_6$ alkyl), —CON($C_1$-$C_6$ alkyl)$_2$, —$CO_2H$, —$CO_2R'$, —OCOR', —OCOR', —OC(=O)OR', —OC(=O)NR', —OC(=S) OR', —OC(=S)NR', a heteroatom, an optionally substituted cycloalkyl, an optionally substituted heterocyclyl, or a combination thereof, wherein each R' is independently selected from hydrogen, alkyl, alkenyl, aryl, heteroaryl a heteroatom, an optionally substituted cycloalkyl, an optionally substituted heterocyclyl, or any combination thereof.

13. The nanoparticle of claim 1, wherein said analyte of interest is a volatile organic compound (VOC) selected from an optionally unsaturated C1-C20 aldehyde, and an optionally unsaturated C1-C20alkane, or both.

14. A chemiresistor sensor comprising:
at least two electrodes; and
a sensing element electrically connected to the two electrodes and comprising a structure made from a plurality of nanoparticles, wherein:
each nanoparticle comprises a metal core in contact with a plurality of ligands bound to said core;
each ligand comprises a first moiety or a salt thereof capable of binding to the core, and an alkyl-aryl moiety covalently bound to said first moiety;
the plurality of ligands are assembled to form a shell on top of said core;
and wherein said nanoparticle is characterized by sensitivity to an analyte of interest comprising a volatile organic compound (VOC) selected from an optionally unsaturated C1-C20 aldehyde, and an optionally unsaturated C1-C20alkane.

15. The chemiresistor sensor of claim 14, wherein the first moiety comprises thio or thiolate, and wherein the alkyl-aryl moiety is represented by Formula 2:

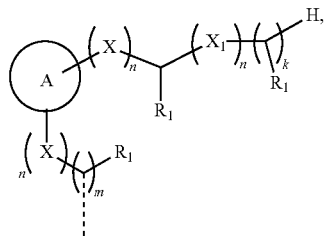

wherein:
each R1 independently represents a substituent or H;
each X and X1 independently represents a heteroatom, or is absent;
A represents an optionally substituted aryl, an optionally substituted heteroaryl, or any combination thereof; the dashed line represents an attachment point to the first moiety;
the heteroatom is selected from the group consisting of O, S, NH, and NR1, or a combination thereof;
n is an integer each independently being 0 or 1;
k is an integer ranging from 0 to 5;
m is an integer ranging from 1 to 5; and if X1 represents the heteroatom then k ranges between 1 and 5.

16. The chemiresistor sensor of claim 14, wherein the ligand comprises at least one of:

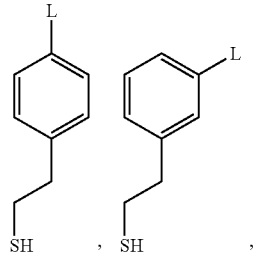

wherein L comprises ethyl or butyl.

17. The chemiresistor sensor of claim 14, wherein the sensor is configured for selective detection of the analyte of interest within a gaseous sample, wherein a concentration of the analyte of interest within the sample is between 1 ppb and 1 ppm.

18. A method for detection of an analyte of interest in a gaseous sample, comprising:
   a. exposing the chemiresistor sensor of claim 14 to the sample comprises a plurality of VOCs;
   b. providing electricity to the sensor, so as to obtain a plurality of conductivity values generated by the sensor; and
   c. analyzing said conductivity values, thereby determining the presence of the analyte of interest within said sample, wherein the analyte of interest comprises a VOC selected from an aldehyde, an alkane or both.

19. The method of claim 18, wherein the analyzing step further comprises determining a concentration of the analyte of interest within the sample.

20. The method of claim 18, wherein a concentration of the analyte of interest within the sample is between 1 ppb and 1 ppm.

\* \* \* \* \*